(12) United States Patent
Pestronk (10) Patent No.: US 9,535,072 B2
(45) Date of Patent: Jan. 3, 2017

(54) ANTIBODIES TO DISULFATED HEPARIN DISACCHARIDE IN THE DIAGNOSIS OF NEUROPATHY

(75) Inventor: Alan Pestronk, St. Louis, MO (US)

(73) Assignee: WASHINGTON UNIVERSITY, St. Louis, MO (US)

(*) Notice: Subject to any disclaimer, the term of this patent is extended or adjusted under 35 U.S.C. 154(b) by 0 days.

(21) Appl. No.: 13/393,612

(22) PCT Filed: Sep. 2, 2010

(86) PCT No.: PCT/US2010/047706
§ 371 (c)(1),
(2), (4) Date: Apr. 2, 2012

(87) PCT Pub. No.: WO2011/028921
PCT Pub. Date: Mar. 10, 2011

(65) Prior Publication Data
US 2012/0183978 A1    Jul. 19, 2012

Related U.S. Application Data

(60) Provisional application No. 61/239,338, filed on Sep. 2, 2009.

(51) Int. Cl.
*A61K 39/395* (2006.01)
*G01N 33/53* (2006.01)
*G01N 33/68* (2006.01)

(52) U.S. Cl.
CPC ....... *G01N 33/6854* (2013.01); *G01N 2400/40* (2013.01); *G01N 2800/28* (2013.01)

(58) Field of Classification Search
None
See application file for complete search history.

(56) References Cited

U.S. PATENT DOCUMENTS

| 6,077,681 | A  | * | 6/2000 | Pestronk | 435/7.92 |
| 6,228,598 | B1 | * | 5/2001 | Pestronk | 435/7.1 |
| 7,175,989 | B2 | * | 2/2007 | Pestronk | 435/7.1 |
| 2004/0038311 | A1 | | 2/2004 | Pestronk | |

FOREIGN PATENT DOCUMENTS

WO    2011/028921 A1    3/2011

OTHER PUBLICATIONS

Conrad, H.E. Heparin-Binding Proteins 1998, pp. 1-4, 9, 18-19, 21.*
Pestronk et al., Sensory Neuropathy With Monoclonal IgM Binding to a Trisulfated Heparin Disaccharide. Muscle & Nerve Feb. 2003, 188-195.*
Kohler & Milstein, "Continuous Cultures of Fused Cells Secreting Antibody of Predefined Specificity", Nature, 1975, 256:495-497.

(Continued)

*Primary Examiner* — Jeffrey Stucker
*Assistant Examiner* — Aurora M Fontainhas
(74) *Attorney, Agent, or Firm* — Polsinelli PC (57) ABSTRACT

Methods aiding in the diagnosis of certain neuropathies are disclosed, in which the titer of antibodies to a disulfated heparin disaccharide is assessed in a test sample from an subject. Also disclosed are apparatus and kits that can be used in the methods of the invention.

12 Claims, 2 Drawing Sheets

(56) References Cited

OTHER PUBLICATIONS

Pestronk, "Lower motor neuron syndromes defined by patters of weekness, nerve conduction abnormalities, and high titers of antiglycolipid antibodies", Ann. Neurol., 1990, vol. 27, No. 3, pp. 316-326.
Pestronk, "Multifocal motor neuropathy." Neurology, 1997, vol. 49, pp. 1289-1292.
Olney, "Consensus Criteria for the diagnosis of Multifocal Motor Neuropathy", Muscle Nerve, 2003, vol. 27, pp. 117-121.
Linhardt, "Production and Chemical Processing of Low Molecular Weight Heparins". Sem. Thromb. Hem., 1999, 3:5-16. PMID 10549711.
Pestronk, "Motor neuropathies and serum IgM binding to NS6S heparin disaccharide or GM1 ganglioside", J Neurol Neurosurg Psychiatry, 2010, 81:726-730.
International Search Report and Written Opinion from related International Application No. PCT/US2010/047706, dated Nov. 1, 2010, 6 pgs.
Office Action from related Japanese Patent Application No. 2012-528052, dated Apr. 8, 2014, 2 pgs.
Willison, "Sugar refining reveals a further specificity for autoantibodies in multifocal motor neuropathy", J Neurol Neurosurg Psychiatry, 2010, pp. 707-708, vol. 81, No. 7.

\* cited by examiner

ANTIBODIES TO DISULFATED HEPARIN DISACCHARIDE IN THE DIAGNOSIS OF NEUROPATHY

FIELD OF THE INVENTION

The present disclosure relates to diagnostic methods and more particularly to methods of diagnosing neuropathy using immunodetection.

BACKGROUND OF THE INVENTION

Distinction between potentially treatable immune motor neuropathies and other disorders of lower motor neurons depends partly on electrodiagnostic evaluations and serum antibody testing. Nerve conduction testing showing motor conduction block at non-entrapment sites along the length of nerves, especially in distal regions, is widely recognized as a marker of the treatable syndrome, multifocal motor neuropathy (MMN). In addition, serum IgM binding to GM1 ganglioside is common in, and has specificity for, multifocal and other immune motor neuropathies. Testing for IgM anti-GM1 antibodies is especially helpful when electrodiagnostic findings of demyelination are equivocal or negative.

Electrophysiological testing, and testing for IgM anti-GM1 antibodies are not however dispositive of neuropathy in a given subject. For example, in most studies the sensitivity of IgM anti-GM1 antibody testing for MMN ranges from only 30% to 50%. Testing for additional antibodies, including IgM binding to GM2 and GalNAc-GD1a gangliosides, can add some sensitivity, but many patients with immune motor neuropathies have no identified associated serum autoantibody. Accordingly, a need remains for improved methods of diagnosing neuropathy, particularly motor neuropathy, as the cause of clinical symptoms in a subject. Because immune motor neuropathies are potentially treatable, a correct differential diagnosis against certain less treatable alternative diagnoses is especially important. A need therefore remains for improved methods for differentially diagnosing such motor neuropathies, thus to promote more timely treatment.

SUMMARY OF THE INVENTION

In one aspect, the present disclosure provides a method of diagnosing a neuropathy in a subject, the method comprising determining in a test sample from the subject the titer of antibody that binds to a disulfated heparin disaccharide, wherein a titer of the antibody to disulfated heparin disaccharide equal to or greater than a reference titer is indicative of the presence of neuropathy in the subject.

In another aspect, the present disclosure provides a method of diagnosing the cause of a muscle weakness in a subject, the method comprising determining in a test sample from the subject the titer of antibody that binds to a disulfated heparin disaccharide, wherein a titer of the antibody to disulfated heparin disaccharide equal to or greater than a reference titer is indicative that a neuropathy is a cause of muscle weakness in the subject.

In still another aspect, the present disclosure provides a method of diagnosing a motor neuropathy in a subject, the method comprising determining in a test sample from the subject the titer of antibody that binds to a disulfated heparin disaccharide, wherein a titer of the antibody to disulfated heparin disaccharide equal to or greater than a reference titer is indicative of the presence of neuropathy in the subject; and conducting an electrophysiological test of the subject for motor conduction block or motor axon loss.

In still another aspect, the present disclosure provides a method of diagnosing the presence of a neuropathy in a subject, the method comprising a) contacting a sample of a disulfated heparin disaccharide with a test sample from the subject, under conditions sufficient to allow antibodies to the disulfated heparin disaccharide, if present in the test sample, to bind to the disulfated heparin disaccharide to form a contacted sample, and b) comparing a titer of anti-disulfated heparin disaccharide antibody in the contacted sample with a reference titer, wherein a titer of anti-disulfated heparin disaccharide antibody in the contacted sample that is equal to or greater than the reference titer is indicative of the presence of neuropathy.

In still another aspect, the present disclosure provides a kit for use in diagnosis of a neuropathy in a subject, the kit comprising an amount of a disulfated heparin disaccharide and an amount of a first detection antibody.

In yet still another aspect, the present disclosure provides apparatus for performing immunoassay detection of antibodies indicative of a neuropathy, comprising a solid phase having an amount of IdoA-GlcNS-6S bound thereto.

BRIEF DESCRIPTION OF THE DRAWINGS

FIG. 2 is a plot showing frequency of IgM binding to NS6S and GM1 ganglioside in different patient groups. High titre IgM binding to NS6S (≥7000) and GM1 ganglioside (≥2000) was more common in motor neuropathies than controls. Horizontal lines represent titres of 7000 for IgM binding to NS6S and 2000 for IgM binding to GM1 ganglioside. Controls for IgM binding to GM1 ganglioside include all 134 CIDP, ALS and sensory neuropathy control patients. ALS, amyotrophic lateral sclerosis; CB+, patients with motor conduction block found in at least one peripheral nerve; CBe, patients with no conduction block; CIDP, chronic immune demyelinating polyneuropathy; Controls, all ALS, CIDP and sensory polyneuropathy controls; Motor PN, motor neuropathy; Sensory PN, sensory polyneuropathy; # Serums, total number of serums tested in each clinical category; # Titres=0, number of serums tested in each clinical category with no reactivity to antigen (NS6S or GM1 ganglioside) and no data points shown on the logarithmic plot.

DETAILED DESCRIPTION

The present disclosure provides methods, a related apparatus, and kits for diagnosing neuropathy, and particularly motor neuropathy in a subject. As used herein, "subject" refers to a mammal capable of suffering from a neuropathy. In an exemplary embodiment, the subject is human. As described herein, the inventors have surprisingly discovered that elevated titers of IgM antibodies to a disulfated heparin disaccharide, particularly a glucosamine-uronic acid heparin disaccharide such as IdoA-GlcNS-6S (NS6S), correlate with the presence of neuropathy, and particularly with motor neuropathy. More specifically, high titers of IgM antibodies to the disulfated heparin disaccharide were found to correlate with the presence of neuropathy in a subject, and high titers were found to be less frequent in patients with sensory neuropathy than in those with motor neuropathy. Advantageously, combining the method of the invention with existing diagnostic methods for motor neuropathy results in a substantial increase in diagnostic sensitivity.

Accordingly, the present disclosure makes available methods for diagnosing neuropathy, especially motor neuropathy. In brief, the methods diagnose the presence of neuropathy in a subject, by assessing a test sample from a subject for the titer of antibodies to a disulfated heparin disaccharide. A high titer of antibodies to the disulfated heparin disaccharide is indicative of the presence of neuropathy.

I. Methods of Diagnosing a Neuropathy

One aspect of the invention encompasses a method of diagnosing a neuropathy or the cause of muscle weakness in a subject. As used herein, "neuropathy" refers to nerve pathology, and may include, but is not limited to, motor neuropathy (pathology of a motor neuron), immune neuropathy (immune system mediated nerve pathology), sensory neuropathy (pathology of a sensory neuron) and immune motor neuropathy (immune system mediated motor neuron pathology).

In one embodiment, the methods are directed toward diagnosing a neuropathy in a subject. Suitable subjects may include subjects suspected of having neuropathy, subjects with clinical signs of neuropathy, subjects at risk for having neuropathy, and subjects with muscle weakness. The methods are useful, in part, for diagnosing neuropathy, especially motor neuropathy, and including multifocal motor neuropathy, Guillain-Barre Syndrome and other treatable immune motor neuropathies.

In general, the method describes determining the titer of antibody that binds to heparin disaccharide in a test sample from the subject.

(a) Heparin Disaccharides

In some embodiments, the titer of antibody that binds to a heparin disaccharide is determined. Non limiting examples of heparin disaccharides may include GlcA-GlcNAc, GlcA-GlcNS, IdoA-2S-GlcN, IdoA-GlcN, IdoA-GlcNS, IdoA(2S)-GlcNS, IdoA-GlcNS(6S), and IdoA(2S)-GlcNS(6S). Abbreviations are as follows: GlcA is glucuronic acid; IdoA is Iduronic acid; IdoA(2S) is 2-O-sulfo-α-L-iduronic acid; GlcNAc is 2-deoxy-2-acetamido-α-D-glucopyranosyl; GlcNS is 2-deoxy-2-sulfamido-α-D-glucopyranosyl; and GlcNS(6S) is 2-deoxy-2-sulfamido-α-D-glucopyranosyl-6-O-sulfate. In preferred embodiments, the heparin disaccharide is a sulfated heparin disaccharide. In another preferred embodiment, the sulfated heparin disaccharide is a disulfated heparin disaccharide. In an exemplary embodiment, the disulfated heparin disaccharide is a glucosamine-uronic acid heparin disaccharide, such as, for example IdoA-GlcNS-6S (NS6S).

The disulfated heparin disaccharide may encompass a component of a polysaccharide (e.g., a glucosamine-uronic acid heparin disaccharide comprising IdoA-GlcNS-6S (NS6S)), or a component of a modified protein or a peptide (e.g., as a side chain), or a component of a modified lipid. In preferred embodiments, an amount of disulfated heparin disaccharide used in the invention may contain the disulfated heparin disaccharide alone, i.e. not as a component of another molecule.

The disulfated heparin disaccharide may be isolated from naturally-occurring sources or chemically synthesized, and may be a component of a protein produced by recombinant methods. In some embodiments, the disulfated heparin disaccharide may be derived from natural heparin. Natural heparin consists of polysaccharide chains of varying lengths. It may be obtained from animal tissues using methods well known in the art. Natural heparin preparations with anticoagulant activities have been prepared from bovine, porcine, human, turkey, whale, dromedary, mouse, lobster, fresh water mussel, clam, shrimp mangrove crab, and sand dollar tissues.

To prepare disulfated heparin disaccharide from heparin, heparin preparations are fractionated or depolymerized. Various methods of heparin depolymerisation may be used in the manufacture of disulfated heparin disaccharide from heparin and are well known in the art. For instance, see Linhardt R J, Gunay N S. (1999). "Production and Chemical Processing of Low Molecular Weight Heparins". Sem. Thromb. Hem. 3: 5-16. PMID 10549711. Nonlimiting methods of heparin depolymerization may include oxidative depolymerisation with hydrogen peroxide, deaminative cleavage with isoamyl nitrite, alkaline beta-eliminative cleavage of the benzyl ester of heparin, oxidative depolymerisation with $Cu^{2+}$ and hydrogen peroxide, beta-eliminative cleavage by the heparinase enzyme, and deaminative cleavage with nitrous acid. In certain situations, depolymerized heparin may be further chemically processed to obtain different disulfated heparin disaccharide species. For example, deaminative cleavage with nitrous acid results in the formation of an unnatural anhydromannose residue at the reducing terminal of the oligosaccharides produced. This can subsequently be converted to anhydromannitol using a suitable reducing agent. Likewise both chemical and enzymatic beta-elimination result in the formation of an unnatural unsaturated uronate residue (UA) at the non-reducing terminal.

In some embodiments, disulfated heparin disaccharide may be prepared from synthetically produced heparin. In other embodiments, disulfated heparin disaccharide may be synthetically prepared. Nonlimiting methods to synthetically prepare heparin or disulfated heparin disaccharide may include chemical or enzymatic processes, or by genetically engineering cells to produce disulfated heparin disaccharide.

(b) Antibody Titers

The method comprises determining the titer of antibody that binds to disulfated heparin disaccharide. The titer of different types of antibodies (i.e., a sum including the amount of more than one type of antibody) may be determined. Alternatively, the amount of one particular type of antibody (e.g., the amount of IgA, IgD, IgE, IgM or IgG antibody) may be determined. In an exemplary embodiment, the titer of IgM antibody that binds to disulfated heparin disaccharide is determined.

According to the methods, the titer of antibody that binds to disulfated heparin disaccharide is determined by contacting an amount of the disulfated heparin disaccharide with a test sample from the subject. The result is a contacted sample, which is a mixture of disulfated heparin disaccharide and the test sample. The contacted sample is maintained under appropriate conditions to allow binding of any anti-disulfated heparin disaccharide antibody that may be present in the sample to the disulfated heparin disaccharide. The terms, "anti-disulfated heparin disaccharide antibody" or "anti-disulfated heparin disaccharide autoantibody", as used herein, refer to antibody that specifically binds to disulfated heparin disaccharide. An antibody that "specifically binds" to a disulfated heparin disaccharide, as used herein, is an antibody that preferentially binds to a disulfated heparin disaccharide, as compared to binding to other similar molecules (e.g., other disaccharides, other sulfated polysaccharides). The contacted sample is then assessed for the presence or absence, or more particularly for the amount, i.e. titer of anti-disulfated heparin disacccharide antibodies.

The titer of antibody, or the presence or absence of antibody, may be determined by a variety of methods using standard techniques, including enzyme-linked immunosorbent assay (ELISA) or other solid phase immunoassays, radioimmunoassay, nephelometry, electrophoresis, immunofluorescence, immunoblot, or other methods (see Ausubel, F. M. et al., eds., Current Protocols in Molecular Biology, John Wiley & Sons, including supplements through 2001, especially units 11.2 (ELISA) and 11.16 (Determination of Specific Antibody Titer)). In one embodiment, the amount (or presence or absence) of antibody is determined by immunoblot assay. In an exemplary embodiment, the titer is determined by ELISA. Detection of the protein using protein-specific antibodies in immunoassays is known to those of skill in the art (see, e.g., Harlow & Lane, Antibodies: A Laboratory Manual (1988), Coligan, Current Protocols in Immunology (1991); Goding, Monoclonal Antibodies: Principles and Practice (2d ed. 1986); and Kohler & Milstein, Nature 256:495-497 (1975). In an exemplary embodiment, the disulfated heparin disaccharide is attached to a solid phase or support, in a manner that optimizes antibody binding to the epitopes, such as by use of a solid support modified to allow covalent linkage of compounds on its surface (e.g., Nunc CovaLink NH microwell ELISA plates) (see, e.g., U.S. Pat. No. 6,077,681, the entire teachings of which are incorporated herein by reference). In another exemplary embodiment, the solid support is a Costar microwell ELISA plate (Nucleopore, Fisher Scientific).

Typically, the amount of antibody that binds to the disulfated heparin disaccharide sample may be determined using a detector antibody that binds to the anti-disulfated heparin disaccharide antibody. Titers of anti-disulfated heparin disaccharide antibodies may be calculated from the amount of detector antibody bound to the anti-disulfated heparin disaccharide antibody, using standard conversion algorithms. For example, if the detector antibody comprises horseradish peroxidase, titers of antibody may be calculated as set forth in A. Pestronk et al., 27 Ann. Neurol. 316 326 (1990), the entire disclosure of which is hereby incorporated by reference.

In one embodiment of the invention, the titer of anti-disulfated heparin disaccharide IgM antibodies in the test sample is compared to the titer of anti-disulfated heparin disaccharide IgM antibodies present in at least one comparable negative and/or one comparable positive control sample.

(c) Test Sample

The method of diagnosing a neuropathy comprises determining the titer of antibody in a test sample. A test sample, as defined herein, is an amount of bodily fluid taken from a subject. Non-limiting examples of bodily fluids include urine, blood, plasma, serum, saliva, semen, perspiration, tears, mucus, and tissue lysates. In an exemplary embodiment, the bodily fluid contained in the test sample is serum.

The bodily fluids of the test sample may be taken from the subject using any known device or method. Non-limiting examples of devices or methods suitable for taking bodily fluid from a mammal include urine sample cups, urethral catheters, swabs, hypodermic needles, thin needle biopsies, hollow needle biopsies, punch biopsies, metabolic cages, and aspiration.

In order to adjust the expected concentrations of the antibodies in the test sample to fall within the dynamic range of the assay, the test sample may be diluted to reduce the concentration of the antibodies prior to analysis. The degree of dilution may depend on a variety of factors including but not limited to the type of assay used to measure the antibodies, the reagents utilized in the assay, and the type of bodily fluid contained in the test sample. Methods of determining the degree of dilution are known in the art.

If the sample comprises isolated antibodies, the isolated antibodies may include a single type of antibody (e.g., IgA, IgD, IgE, IgG or IgM antibodies), all types of antibodies; or alternatively, two or more types of antibodies (e.g., IgM antibodies, IgG antibodies, or IgM and IgG antibodies) may be isolated. In an exemplary embodiment, the test sample is a sample comprising IgM antibodies from the subject.

(d) Diagnosing a Neuropathy

According to the methods, the titer of antibody that binds to a disulfated heparin disaccharide is determined, wherein a titer of the antibody to disulfated heparin disaccharide equal to or greater than a reference titer is indicative of the presence of neuropathy in the subject. Alternatively, in a subject having muscle weakness, a titer of the antibody to disulfated heparin disaccharide equal to or greater than a reference titer is indicative that a neuropathy is a cause of muscle weakness in the subject.

The reference titer is an amount of the same type of antibody as the antibody assessed in the contacted sample: for example, if the sum of the amount of different types of antibodies (i.e., including more than one type of antibody) for the contacted sample is compared to the reference titer, the sum of the amount of those types of antibodies is also used for the reference titer. If the amount of one particular type of antibody (e.g., the amount of IgM or IgG antibodies) in the contacted sample is compared with the reference titer, the amount of that type of antibody is also used for the reference titer.

The reference titer refers to an amount of anti-disulfated heparin disaccharide antibodies that correlates with a diagnosis of neuropathy. A reference titer may be determined, by comparing amounts of anti-disulfated heparin disaccharide antibodies in contacted samples from subjects known to have a neuropathy (e.g., a "positive control sample"), with amounts of anti-disulfated heparin disaccharide antibodies in contacted samples from subjects known not to have a neuropathy (e.g., a "negative control sample" as described below), and determining what titer of antibody correlates with disease. The reference titer may be determined by determining the amounts of antibodies in positive and/or negative control samples concurrently with determining the amount of antibodies in the contacted sample. Alternatively, the reference titer may be a historically determined amount (i.e., an amount determined prior to determining the amount of antibodies in the contacted sample). For example, in one embodiment, a reference titer may be a titer of anti-disulfated heparin disaccharide antibody in the test sample that statistically is significantly greater than the titer of anti-disulfated heparin disaccharide antibody in comparable control sample(s), such as an amount that is at least about two standard deviations above, preferably three or more standard deviations above, and even more preferably four or more standard deviations above, the amount of anti-disulfated heparin disaccharide antibody in comparable negative control samples. In a preferred embodiment, the reference titer for an amount of anti-disulfated heparin disaccharide antibody in the test sample is at least about 2000, 3000, 4000, 5000, 6000, 7000, 8000, or 9000. In an exemplary embodiment, the reference titer for an amount of anti-disulfated heparin disaccharide antibody in the test sample is at least about 7,000.

In alternative embodiments, the amount of anti-disulfated heparin disaccharide antibody in the contacted sample may be compared with the amount of anti-disulfated heparin disaccharide antibody in at least one comparable negative control sample (i.e., a sample from a subject who is not affected by a neuropathy). The negative control sample may be a sample from any subject who is not affected by a neuropathy. It is not necessary that the negative control sample be from a subject who is free of disease: for example, the negative control sample can be a sample from a subject who has another nervous system disorder, particularly a disorder with clinical symptoms of motor dysfunction such as multiple sclerosis. A "comparable" negative control sample is a sample of the same type of body fluid or tissue as the test sample; alternatively, if the test sample includes antibodies isolated from a sample of fluid or tissue, the comparable negative control sample is a sample of antibodies isolated from the same type of bodily fluid or tissue. More than one control sample may be used. The assay of the negative control sample determines the same type of antibody as the assay of the contacted sample: for example, if the sum of the amount of different types of antibodies (i.e., including more than one type of antibody) is detected for the contacted sample, the sum of the amount of those types of antibodies is also determined for the negative control sample. If the assay determines the amount of one particular type of antibody (e.g., the amount of IgM or IgG antibodies) in the contacted sample, the amount of that type of antibodies is also determined for the negative control sample. In an exemplary embodiment, more than one control sample are used.

The presence of an amount of anti-disulfated heparin disaccharide antibody in the test sample that is significantly greater than the amount of anti-disulfated heparin disaccharide antibody in a comparable negative control sample correlates with the presence of a neuropathy. The presence of an amount of anti-disulfated heparin disaccharide antibody in the test sample that is equal to or greater than a comparable positive control sample(s), correlates with the presence of a neuropathy.

In an exemplary embodiment, an amount of anti-disulfated heparin disaccharide antibody in the test sample that is "significantly greater" is an amount that is at least about two standard deviations above the amount of anti-disulfated heparin disaccharide antibody in comparable control samples, and is preferably two or more standard deviations above; more preferably three or more standard deviations above; and even more preferably, four or more standard deviations above. For example, if the titer of both IgM and IgG antibody is measured, an amount of the combination of anti-disulfated heparin disaccharide IgM antibody and anti-disulfated heparin disaccharide IgG antibody that is equal to, or greater than, two standard deviations above the amount of the combination of anti-disulfated heparin disaccharide IgM antibody and anti-disulfated heparin disaccharide IgG antibody in comparable control samples is "significantly greater" and therefore correlates with neuropathy. In another example, if titer is used, a titer of anti-disulfated heparin disaccharide antibody, particularly anti-disulfated heparin disaccharide IgM antibody, in the test sample that is equal to, or greater than, three standard deviations above the titer of anti-disulfated heparin disaccharide antibody in comparable control samples, correlates with a diagnosis of neuropathy.

If desired, and as generally recognized in the art, when determining the amount of anti-disulfated heparin disaccharide antibody, the amount of one or more control antibodies present in the sample may be subtracted from the detected amount of anti-disulfated heparin disaccharide antibody, in order to yield a corrected amount of anti-disulfated heparin disaccharide antibody. For example, in one embodiment, an amount of antibody to a control disaccharide, such as a different uronic acid-glucosamine disaccharide, may be subtracted from the detected amount of anti-disulfated heparin disaccharide antibody.

(e) Further Diagnosis

The method of the invention is applicable when no other indicators of motor neuropathy are present in the subject, and also when one or more other indicators of motor neuropathy are also present in the subject. The other indicators may include, for example, muscle weakness in the subject, and/or electrophysiological testing results showing evidence of motor conduction block or motor axon loss in at least one location. Another indicator of motor neuropathy may be from other antibody testing. For example, another indicator of motor neuropathy can be a high titer of IgM binding to GM1 ganglioside as determined from a test sample from the subject, as previously described for example in A. Pestronk & R. Choksi, 49 Neurology 1289-92 (1997), the entire disclosure of which is hereby incorporated by reference.

In some embodiments, the results of antibody testing are combined with the results of one or more clinical indicators or tests of motor function, e.g. clinical evidence of muscle weakness in the individual, or electrophysiological testing establishing motor conduction block in at least one location, or other evidence of motor axonal loss.

In other embodiments, the methods may further advantageously include determining in the test sample from the subject the titer of IgM antibodies that bind to GM1 ganglioside, wherein a titer of IgM antibodies that bind to GM1 ganglioside that is greater than or equal to a second reference titer correlates positively with presence of motor neuropathy in the subject. As previously described, serum IgM binding to GM1 ganglioside is common in, and has specificity for, multifocal and other immune motor neuropathies. (See, e.g., Olney et al., 27 Muscle Nerve 117-21 (2003)). A suitable reference titer for serum IgM binding to GM1 ganglioside, i.e. second reference titer, is a titer of at least about 2,000. Thus, serum antibody testing that determines "high" antibody binding to a disulfated heparin disaccharide with reference to a first reference titer, and to GM1 ganglioside with reference to a second reference titer, correlates positively with presence of motor neuropathy in the subject.

II. Kits

The present disclosure also includes kits and related apparatus that may be used according to the methods of the invention. For example, a kit for use in diagnosis of a neuropathy in a subject may comprise an amount of a disulfated heparin disaccharide, for example a glucosamine-uronic acid heparin disaccharide such as IdoA-GlcNS-6S, and an amount of a first detection antibody. The detection antibody may typically be a labeled antibody that binds to antibody, preferably to the anti-disulfated heparin disaccharide antibody, and even more preferably, to anti-disulfated heparin disaccharide IgM antibody. The detection antibody may comprise an antibody bound to a detectable label, such as an enzyme, radioactive molecule, or fluorescent agent. If the detector antibody is bound to an enzyme that reacts with an added substrate to yield a colored product, such as horseradish peroxidase, the kit may also include the substrate as well. The disulfated heparin disaccharide in the kit may be adhered to a solid phase or support, which may be for example a cuvette, beads, or a plate such as those typically used for ELISA, e.g. a macrowell plate or a microtiter plate. In an exemplary embodiment the solid phase is a Costar microwell ELISA plate, and the disulfated heparin disaccharide is covalently bound to microwells of the plate. For example, IdoA-GlcNS-6S may be covalently linked to suitable chemical moieties adhered to the solid phase, for example to the microwells of a plate. This may be accomplished by adding a suitable compound, for example with secondary amino groups such as N-(3-dimethylamino-propyl)-N-ethyl-carbodiimide, in solution to the microwells before adding the antigen to the plates. The antigen is then added to the microwells and incubated under conditions and for a time sufficient to permit covalent bonding of the disulfated heparin disaccharide to the chemical moieties adhered to the plate. In another embodiment, the kit may further include an amount of GM1 ganglioside and an amount of a second detection antibody. As with the first detection antibody, the second detection antibody will typically include a detectable label and preferably binds to human IgM antibody. Both the GM1 ganglioside and the IdoA-GlcNS-6S may be bound to a solid phase. The GM1 ganglioside may be covalently bound to a solid phase, for example a microwell ELISA plate as described for example in Alan Pestronk & R. Choksi, 49 Neurology 1289-1292 (1997). In an exemplary embodiment the solid phase is a Costar microwell ELISA plate.

EXAMPLES

The following Examples are offered for the purpose of illustrating the present disclosure and are not to be construed as limiting of the scope of the claims. The disclosures of all references cited herein are hereby incorporated by reference in their entireties.

Materials and Methods for Examples 1-6

Patient and serum samples: Subjects for evaluation of serum IgM binding were retrospectively identified from a clinical database of patient diagnoses without knowledge of results of prior antibody testing. The 75 patients were identified were diagnosed by their physicians as having acquired chronic motor neuropathies and then met several additional inclusion and exclusion criteria. All were required to have had clinical, electrodiagnostic and laboratory evaluation in the neuromuscular centre at Washington University in St Louis and have serum available for ELISA studies. All patients had at least one limb with: (1) neuropathic weakness in the distribution of two or more peripheral nerves without anatomical explanations for the weakness; and (2) normal sensory function by clinical and electrodiagnostic testing. Patients were excluded if they had a family history of a similar disorder, cranial nerve or bulbar weakness, upper motor neuron signs, rapidly progressive disease leading to inability to walk or death during the first 3 years after symptom onset or disabling sensory loss. The exclusion criteria eliminated four patients. No patients from a previous ELISA study of IgM anti-GM1 antibodies in MMN9 were included in this study. Charts were reviewed in the 75 patients with motor neuropathies without reference to antibody status. Clinical and electrodiagnostic features, including conduction block and serum M proteins (72 patients tested by immunofixation) were documented. Electrodiagnostic studies usually included nerve conduction studies of at least six motor nerves, including four in the upper extremity, and three sensory nerves. Fewer nerves were studied in some patients with multiple conduction blocks. Conduction block along very proximal nerve segments was not routinely tested for, and was not considered in patient subclassifications. EMG studies were available in 60 patients, with paraspinous evaluation in 25. Disease control patients were selected from our clinical database from the past 3 years based only on diagnosis and serum availability. Records were reviewed to confirm diagnoses. Diagnoses included the following: definite amyotrophic lateral sclerosis (ALS, 50 patients); chronic immune demyelinating polyneuropathy (CIDP, 28 patients); and sensory neuropathy (56 patients). Sensory neuropathy patients had distally predominant reduced sensation and normal strength. Two sensory neuropathy patients had demyelinating neuropathies and IgM binding to MAG. Six others had axonal sensory neuropathies with serum IgM binding to trisulphated heparin disaccharide (TS-HDS). Nine patients with sensory neuropathy also had diabetes. The other 39 were idiopathic. From 2002 to 2009, all serums submitted to the Neuromuscular Clinical Laboratory at Washington University were tested for IgM binding to GM1 ganglioside, including 2113 different patients clinically evaluated in the neuromuscular centre. To examine the specificity of IgM anti-GM1 serum testing, the records of the 27 patients from the centre we reviewed with positive results. The Washington University Human Studies Committee approved all procedures. Informed consent was not required.

Figure 1:
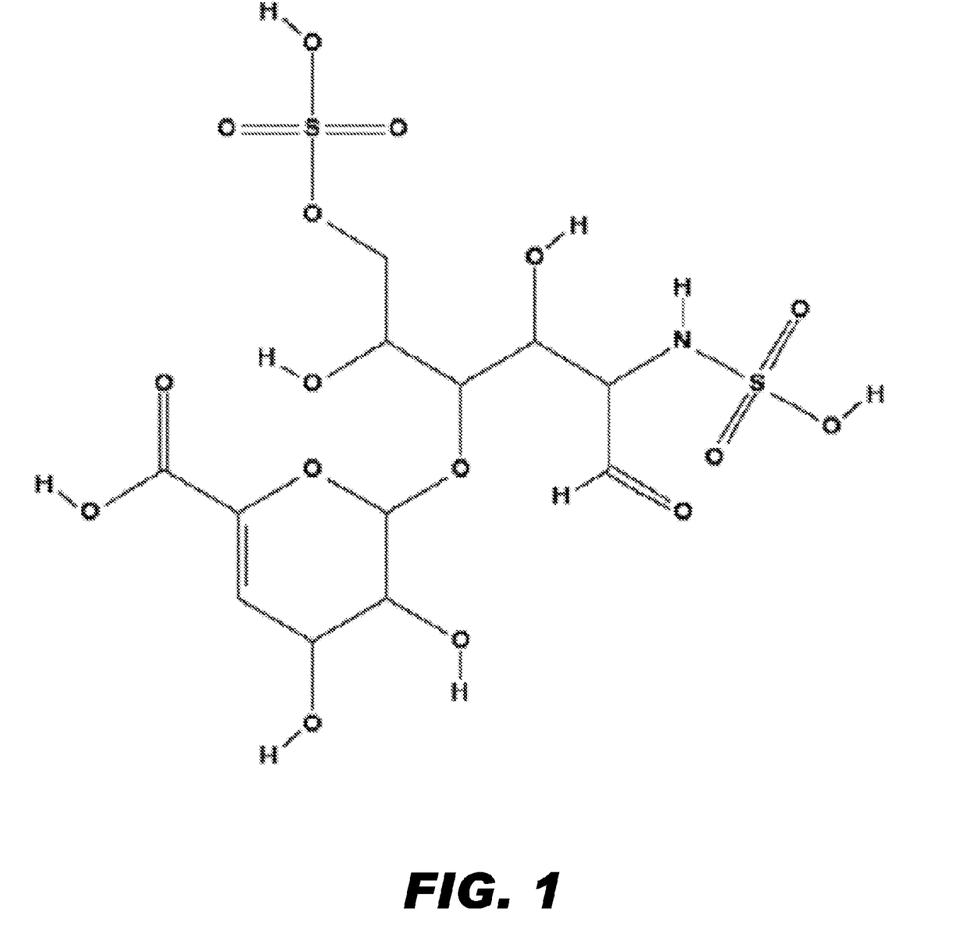
FIG. 1 shows the molecular structure of the disulfated heparin disaccharide NS6S (α-4-deoxy-I-threohex-4-enopyranosyluronic acid-[1-4]-d-glucosamine-S-6S; "IdoA-GlcNS-6S").

Assays for IgM binding to NS6S and GM1 ganglioside: NS6S is a-4-deoxy-I-threohex-4-enopyranosyluronic acid-[1-4]-dglucosamine-S-6S (IdoA-GlcNS-6S; Sigma H1020) (FIG. 1). NS6S contains two sugar moieties, L-iduronic acid linked to D-glucosamine and two sulphate groups. The sulphate groups are linked to the D-glucosamine moiety, one N-linked and another O-linked at position six. Other antigens tested in preliminary ELISA evaluations were sulphatide (purified from Sigma S-1006) and heparin disaccharides TS-HDS (IdoA-2S-GlcNS-6S; Sigma H9267), 10 IdoA-2S-GlcNS (Sigma H9392), IdoA-2S-GlcN-6S (Sigma H8892), IdoA-2S-GlcN (Sigma H9142), IdoA-GlcN-6S (Sigma H9017), IdoA-GlcNS (Sigma H1145) and IdoA-GlcN (Sigma H9276). Serums were assayed, using ELISA methodology with covalent antigen linkage to plates, as previously described for antiganglioside antibodies. Costar microwell ELISA plates (Stripwell-Amine 2388; Corning N.Y. USA) were used for NS6S and other disaccharides, CovaLink NHmicrowell ELISA plates (Nunc, Roskilde, Denmark) for GM1 ganglioside and Immulon 2HB (Thermo, Milford, Mass., USA) for preliminary studies with sulphatide and some other antigens. To measure serum IgM binding to NS6S, 1.25 mg of NS6S dissolved in 50 ml of 0.05% N-hydroxysuccinamide was used per well. Levels of selective binding to NS6S were calculated by subtracting levels of IgM binding to GD1a ganglioside, an antigen that is used in the laboratory to calculate background IgM binding for many carbohydrate containing antigens. High titres of selective IgM binding to NS6S ($\geq 7000$) were greater than 4 SDs above the mean of a separate initial series of tests in serums from 10 patients with ALS and 10 control subjects. High titres of IgM binding to GM1 ganglioside were $\geq 2000$, the criterion used for these antibodies in our Neuromuscular Clinical Laboratory.

Statistics: $X^2$ and t tests were generally used to calculate the significance of differences between diagnostic groups. Fisher's exact tests were used to calculate the significance of differences within the motor neuropathy group. Patients with missing data were excluded from that analysis only. AP performed the statistical analysis. Results are expressed as mean+/−SE.

Example 1

Clinical and Electrodiagnostic Features in Motor Neuropathy Patients

In the series of motor neuropathy patients ascertained from the clinical database, most had asymmetric, distal and arm predominant weakness (Table 1). Seventy-two motor neuropathy patients had weakness in two or more limbs that had normal sensation on clinical examination. Onset ages ranged from 23 to 76 years with a mean of 46+/−2 years. Clinical sensory testing was abnormal in the arms in two patients. Both had distal predominant reduction in pin sensation in an arm with weakness but normal electrodiagnostic sensory testing. Clinical testing was abnormal for pin or vibration sensation in the legs in 28 patients, 26 of whom had distal predominant, bilateral, symmetric loss in the legs with normal strength. Distal sensory loss on clinical examination of the legs was present more often (p=0.0003) in patients aged more than 50 years (68%) than in younger patients (22%). Motor conduction block was present in 56% (42 of 75), and full clinical and electrodiagnostic criteria for MMN in 31% (23 of 75), of motor neuropathy patients. Among the 33 patients with no conduction block, three had other clear features of demyelination (one each with slowed nerve conduction velocities, prolonged distal latencies and temporal dispersion) while 30 had motor axon loss without evidence of demyelination on distal nerves. Sural sensory nerve action potentials were absent, or had reduced amplitude, in 16 patients. On EMG, acute or chronic denervation changes in muscles in weak limbs were present in 55 of 60 patients tested. The five patients with no denervation on EMG all had focal conduction block in at least one location. Thoracic paraspinous denervation was found in 11 of the 25 patients tested.

TABLE 1

Motor Neuropathy Patient Characteristics

|  | number of patients | Percent of patients |
| --- | --- | --- |
| Weakness | 75 | 100 |
| Distal | 73 | 97 |
| Distal predominant | 70 | 93 |
| Asymmetric | 70 | 93 |
| Arms | 73 | 97 |
| Arm predominant | 71 | 95 |
| Leg predominant | 2 | 3 |
| MMN signs | 23 | 31 |
| Conduction block | 42 | 56 |
| Conduction block, or IgM versus GM1 or NS6S | 62 | 83 |
| Sensory loss, legs | 28 | 37 |
| SNAPs abnormal, legs | 16 | 21 |
| IgM M-protein | 17 | 23 |

Clinical and laboratory features in the motor neuropathy group (75 patients). Most patients had distal, asymmetric, arm predominant weakness.
Conduction block, motor conduction block found in at least one location at a nonentrapment site along the length of a nerve;
Conduction block, or IgM versus GM1 or NS6S, presence of at least one of motor conduction block or high titre IgM binding to NS6S or GM1 ganglioside;
IgM M-protein, IgM M-protein present in serum detected by immunofixation methodology;
MMN, multifocal motor neuropathy, consensus criteria;
SNAPs abnormal, sensory nerve action potentials absent or reduced amplitude.

Example 2

Preliminary ELISA Testing

Comparison of 18 motor neuropathy serums for IgM binding to disaccharides and sulphatide showed that the highest titres were obtained using the NS6S disaccharide. Two other antigens with at least two sulphate moieties, IdoA-2S-GlcNS and TS-HDS, gave titres that averaged approximately 70% of NS6S. All other antigens tested gave titres that averaged less than 50% of NS6S. The lowest titres, within control ranges, were found with sulphatide and non-sulphated disaccharides. IgM binding to NS6S was not higher than controls when tested with the antigen added to Immulon or Covalink ELISA plates.

Example 3

IgM Binding to NS6S in Motor Neuropathies and Controls

Figure 2:
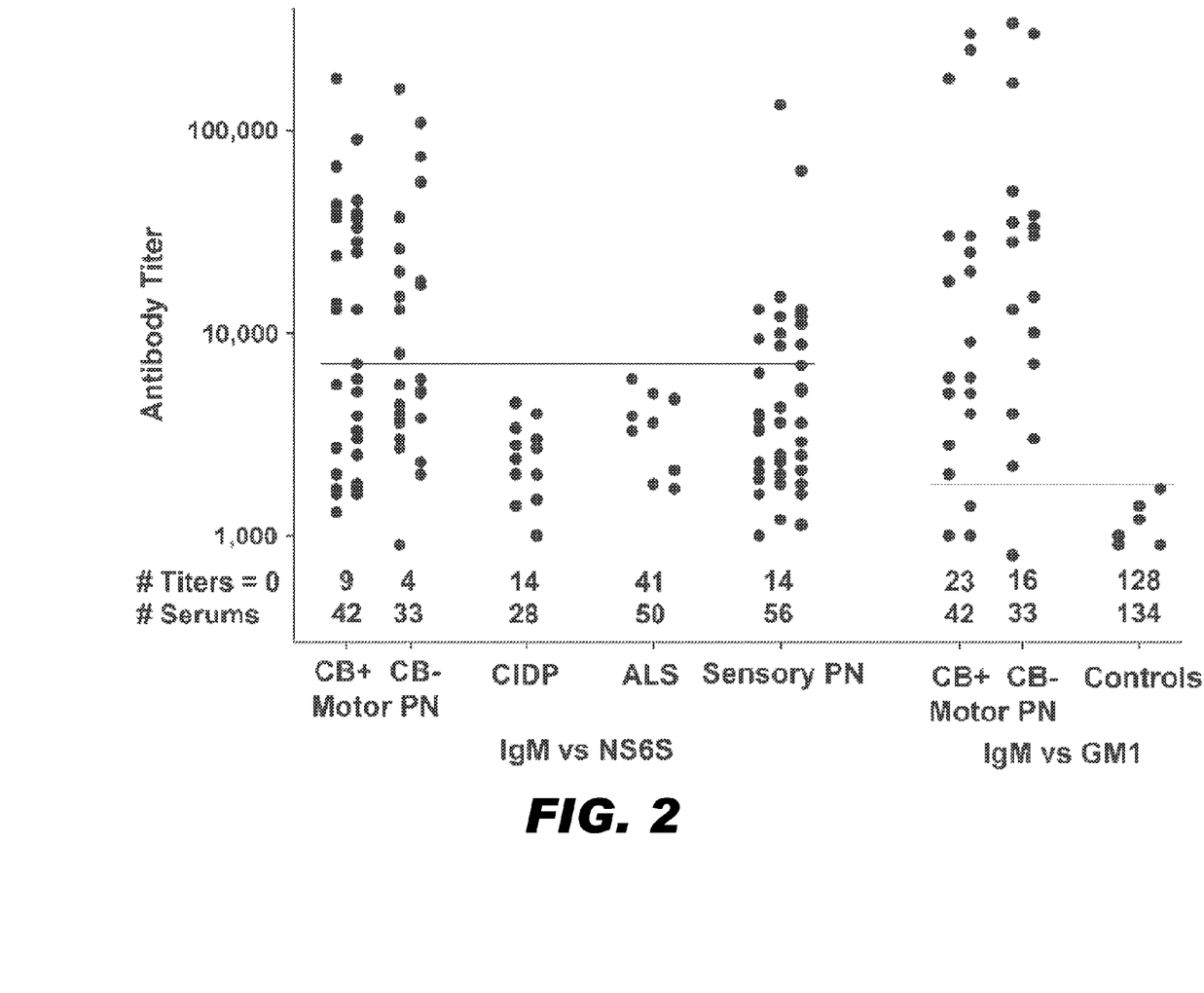

High titres of serum IgM binding to NS6S (≥7000) were found in 43% of motor neuropathy patients and ranged from 7000 to 180 000 (FIG. 2). High titre IgM binding to NS6S occurred more commonly in motor neuropathy patients than in the overall disease control group ($p<10^{-6}$). No patient in the control groups with ALS or CIDP had high titre IgM binding to NS6S. High titres of IgM binding to NS6S were less frequent (p=0.01) in sensory neuropathy patients than in the motor neuropathy group. Levels of IgM binding to NS6S were higher (p=0.003) in the motor neuropathy group (mean 20 18063854) than in the sensory neuropathies (mean 623062393). The sensory neuropathy serum with the highest titre of IgM binding to NS6S also had very high titre IgM binding to MAG (90 000).

Example 4

IgM Binding to GM1 Ganglioside or NS6S in Motor Neuropathies and Controls

High titres of IgM binding to GM1 were present in 43% of motor neuropathy patients. No patient with ALS, CIDP or sensory neuropathy had high titres of serum IgM binding to GM1 ganglioside. High titres of IgM binding to at least one of NS6S or GM1 ganglioside were present in 64% (48 of 75) of motor neuropathy patients. High titres of IgM binding to both NS6S and GM1 were present in 21% (16 of 75) of motor neuropathy patients, and to NS6S only or GM1 only in 21% (16 of 75) each. High titres of IgM binding to NS6S were not more frequent (p=0.25) in serums with IgM binding to GM1 (52%) than without (36%).

Example 5

IgM Antibodies in Relation to Other Motor Neuropathy Patient Features

Either motor conduction block or IgM antibody binding to NS6S or GM1 ganglioside was found in 83% (62 of 75) of motor neuropathy patients. The frequency and titres of IgM binding to NS6S and GM1 were similar (p=0.5) in subgroups of motor neuropathy patients with and without motor conduction block (Table 2). Titres of IgM binding to NS6S and GM1 averaged 19 042+/−4945 and 20 730+/−9696 in motor neuropathy patients with conduction block and 21 664+/−6184 and 32 703+/−14 036 without conduction block. Frequencies and titres of IgM binding to NS6S and GM1 were not different in patients with and without criteria for MMN. There was a trend (p=0.08) towards a reduced frequency of high titre IgM binding to GM1 ganglioside in full criteria MMN compared with other motor neuropathy patients. Frequencies of high titre IgM binding to NS6S and GM1 ganglioside were similar in patients with and without paraspinous denervation, distal sensory loss or abnormal sensory nerve action potentials (SNAPs). The frequency of high titre IgM binding to NS6S or GM1 was higher (p=0.0001) in patients with serum IgM M-proteins than in those with no IgM M-protein.

TABLE 2

NS6S and GM1 antibody associations

|  | N | NS6S+ N+ | NS6S+ %+ | GM1+ N+ | GM1+ %+ | NS6S+ or GM1+ N+ | NS6S+ or GM1+ %+ |
|---|---|---|---|---|---|---|---|
| All MN serums | 75 | 32 | 43 | 32 | 43 | 48 | 64 |
| CB+ | 42 | 18 | 43 | 16 | 38 | 28 | 67 |
| CB– | 33 | 14 | 42 | 16 | 48 | 20 | 61 |
| Axon loss only | 30 | 12 | 40 | 13 | 43 | 17 | 57 |
| Sensory loss, legs | 28 | 13 | 46 | 12 | 43 | 18 | 64 |
| SNAPs abnormal | 16 | 4 | 25 | 9 | 56 | 10 | 63 |
| Paraspinous den | 11 | 6 | 55 | 7 | 64 | 8 | 73 |
| Igm M-prot+ | 17 | 12 | 71 | 14 | 82 | 17 | 100 |
| IgM M-prot– | 55 | 19 | 35 | 15 | 27 | 28 | 51 |
| CIDP | 28 | 0 | 0 | 0 | 0 | 0 | 0 |
| ALS | 50 | 0 | 0 | 0 | 0 | 0 | 0 |
| Sensory PN | 56 | 12 | 21 | 0 | 0 | 12 | 21 |

CIDP - Chronic immune demyelinating polyneuropathy;
ALS = Amyotrophic lateral sclerosis;
Sensory PN = Sensory polyneuropathy.
IgM binding to NS6S and GM1 ganglioside were similarly common in motor neuropathy patients. They were occasionally present, or absent, in other disease control patient groups. They were more common in motor neuropathy patients with IgM M-proteins (p = 0.0001) but were similarly common in groups with and without motor conduction block.
%+, percent of patients tested positive;
ALS, amyotrophic lateral sclerosis;
CIDP, chronic immune demyelinating polyneuropathy;
GM1+, patients with high titres (≥2000) of serum IgM binding to GM1 ganglioside;
IgM M-protein+, IgM M-protein present in serum detected by immunofixation methodology;
IgM M-proteine, IgM M-protein not found in serum by immunofixation methodology;
IVIg, intravenous immunoglobulin;
MN, motor neuropathy;
N, number of patients;
N+, number of patients positive;
NS6S+, patients with high titres (≥7000) of serum IgM binding to NS6S disaccharide;
Paraspinous den, denervation found on EMG in thoracic paraspinous muscles;
Sensory PN, sensory polyneuropathy;
SNAPs abnormal, sensory nerve action potentials absent or reduced amplitude.

Example 6

Clinical Features in Patients with Positive Testing Serum Testing for IgM Binding to GM1

Review of the 2113 serums from clinic patients obtained over a 7 year period revealed 27 patients with high titres of IgM binding to GM1. Of the positive results, 24 were from patients with motor neuropathies who are included in this series, one had slowly progressive, unilateral hand weakness with motor axon loss but no demyelination and a diagnosis of monomelic amyotrophy, and two had mild idiopathic axonal, symmetric sensory polyneuropathies with predominant involvement of the legs. These two patients were the only ones of the 27 GM1 positive serums or of the collection of 75 motor neuropathy patients who also had high titres of IgM binding to sulphatide.

Example 7

IgM Binding to NS6S in Guillain-Barre Syndrome

IgM antibodies from 30% of patients with Guillain-Barre Syndrome were also found to bind NS6S using methods described in the examples above.

What is claimed is:

1. A method of diagnosing a motor neuropathy in a subject, comprising:
   (a) incubating a test sample from the subject with disulfated heparin disaccharide immobilized on a solid phase,
   (b) contacting the test sample and disulfated heparin disaccharide with a detection antibody, wherein the detection antibody is detectably labeled and binds to human antibody, and
   (c) detecting the titer level of the detection antibody indirectly bound to the solid phase, wherein a titer level of detection antibody equal to or greater than a positive control reference titer is indicative of the presence of a motor neuropathy in the subject, wherein the detection antibody binds to human IgM antibodies.

2. The method of claim 1, wherein the motor neuropathy is multifocal motor neuropathy.

3. The method of claim 1, wherein the motor neuropathy is immune-mediated motor neuropathy.

4. The method of claim 1, wherein the motor neuropathy is Guillain-Barre syndrome.

5. The method of claim 1, wherein the subject has weakness.

6. The method of claim 1, wherein the subject has electrophysiological evidence of motor conduction block, motor axon loss, or electrophysiological evidence of both motor conduction block and motor axon loss.

7. The method of claim 1, further comprising conducting an electrophysiological test of the subject for motor conduction block or motor axon loss.

8. The method of claim 1, further comprising detecting in the test sample from the subject a titer of IgM antibodies that bind to GM1 ganglioside.

9. The method of claim 1, wherein the disulfated heparin disaccharide is a glucosamine-uronic acid heparin disaccharide.

10. The method of claim 1, wherein the disulfated heparin disaccharide is IdoA-GlcNS-6S.

11. The method of claim 1, wherein the positive control reference titer is at least about 7,000.

12. The method of claim 1, wherein the detection antibody is detectably labeled with an enzyme, radioactive molecule, or fluorescent agent.

\* \* \* \* \*

UNITED STATES PATENT AND TRADEMARK OFFICE
CERTIFICATE OF CORRECTION

| | | |
|---|---|---|
| PATENT NO. | : 9,535,072 B2 | Page 1 of 1 |
| APPLICATION NO. | : 13/393612 | |
| DATED | : January 3, 2017 | |
| INVENTOR(S) | : Pestronk | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 487 days.

Signed and Sealed this
Twenty-first Day of November, 2017

Joseph Matal
*Performing the Functions and Duties of the*
*Under Secretary of Commerce for Intellectual Property and*
*Director of the United States Patent and Trademark Office*